(12) United States Patent
Nonomura et al.

(10) Patent No.: US 8,133,991 B2
(45) Date of Patent: Mar. 13, 2012

(54) ALLERGEN INACTIVATING AGENT

(75) Inventors: Mami Nonomura, Tochigi (JP); Kimihiko Hori, Tochigi (JP); Hiroshi Nojiri, Tochigi (JP); Hiroyuki Yanagida, Tokyo (JP); Fumiko Okuda, Tochigi (JP)

(73) Assignee: Kao Corporation, Tokyo (JP)

( * ) Notice: Subject to any disclaimer, the term of this patent is extended or adjusted under 35 U.S.C. 154(b) by 1558 days.

(21) Appl. No.: 11/045,328

(22) Filed: Jan. 31, 2005

(65) Prior Publication Data

US 2005/0197319 A1 Sep. 8, 2005

Related U.S. Application Data

(63) Continuation-in-part of application No. 10/519,474, filed as application No. PCT/JP03/08390 on Jul. 2, 2003.

(30) Foreign Application Priority Data

Jul. 3, 2002 (JP) .................................. 2002-194588

(51) Int. Cl.
*C07H 1/00* (2006.01)
*C08B 31/08* (2006.01)
*C08B 11/08* (2006.01)
*A61K 31/715* (2006.01)

(52) U.S. Cl. ............ 536/124; 536/95; 536/96; 536/111; 514/57; 514/54

(58) Field of Classification Search ............ 536/95, 536/96, 111, 124; 514/54, 57
See application file for complete search history.

(56) References Cited

U.S. PATENT DOCUMENTS 6,541,614 B1 4/2003 Nagasawa et al.
6,800,247 B1 * 10/2004 Suh et al. .......................... 422/28

FOREIGN PATENT DOCUMENTS

| JP | 58-135805 | 8/1983 |
| JP | 2001-269518 | 10/2001 |
| JP | 2002-146383 | 5/2002 |
| WO | WO 91/10434 | 7/1991 |
| WO | WO 96 22044 | 7/1996 |
| WO | 00 73351 | 12/2000 |
| WO | WO 00/73351 A1 * | 12/2000 |
| WO | WO 02 28179 | 4/2002 |

OTHER PUBLICATIONS

Luczynska et al ("A two-site monoclonal antibody ELISA for the quantification of the major Dermatophagoides spp. allergens, Der p I and Der f I", Journal of Immunological Methods, 118 (1989) 227-235).*

* cited by examiner

*Primary Examiner* — Shaojia Anna Jiang
*Assistant Examiner* — Everett White
(74) *Attorney, Agent, or Firm* — Oblon, Spivak, McClelland, Maier & Neustadt, L.L.P.

(57) ABSTRACT

An allergen inactivating agent is provided which has no adverse effects on the human body and which does not cause problems such as color development.
An allergen inactivating agent containing a polysaccharide derivative as its effective component, wherein said polysaccharide derivative has a cellulose ether or a starch ether as its backbone, and some or all of hydrogen atoms in the hydroxy group of the polysaccharide derivative are substituted by a group represented by the following general formula (1):

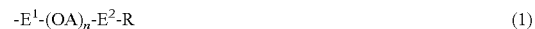

$$-E^1-(OA)_n-E^2-R \qquad (1)$$

wherein $E^1$ represents an alkylene containing 1 to 6 carbon atoms optionally substituted with hydroxy group or oxo group; n represents a number of 0 to 50; A independently represents an alkylene containing 1 to 6 carbon atoms, the number of A being n; $E^2$ represents ether bond or oxycarbonyl group; R represents an alkyl group containing 4 to 30 carbon atoms optionally substituted with hydroxy group, a sulfoalkyl group containing 1 to 5 carbon atoms optionally substituted with hydroxy group, or a salt thereof.

9 Claims, 2 Drawing Sheets

ALLERGEN INACTIVATING AGENT

TECHNICAL FIELD

This invention relates to an allergen inactivating agent for inactivating allergens in environment.

Recently, allergic diseases such as atopic dermatitis, allergic rhinitis, and asthma are increasing, and such diseases have become an important social problem. One cause for such increase in the allergic diseases is increase of the environmental allergen. In particular, improvement of air tightness of houses has created an ideal condition for mite propagation in the indoor space, and increase in the amount of mite allergen and other allergens in the indoor space has become a serious problem.

Removal of such allergen is a rational means for preventing and treating allergic diseases, and attempts have been made to prevent contact between human and the allergen by using an air cleaner, a highly air tight mattress cover, and the like. The effects, however, have not been sufficient.

Attempts have also been made to inactivate mites by using miticides. Use of such miticides, however, is associated with the risk of adversely affecting human body, and killing of the mites is not the fundamental way of reducing the amount of allergen since feces and corpse remaining after the killing of the mites are allergic.

Attempts have also been made to inactivate the mites by using a repellent. Use of such repellent, however, is associated with the problem of insufficient sustainability of the effects. The mite may recover after a while, and even if the number of mites could be reduced, remaining feces and dead body have antigenicity, therefore use of such repellent is not a fundamental way of reducing the amount of the antigen.

Chemical inactivation of the allergen by natural extracts such as tea extract and tannic acid has also been attempted. However, such inactivation is associated with the problem of color development by chemical change with time as well as safety problem when the chemical substance is used in a large amount, therefore use of such chemical substance in a commercial product has been difficult.

SUMMARY OF THE INVENTION

This invention relates to an allergen inactivating agent containing a polysaccharide derivative as its effective component, wherein said polysaccharide derivative has a cellulose ether or a starch ether as its backbone, and some or all of hydrogen atoms in the hydroxy group of the polysaccharide derivative are substituted by a group represented by the following general formula (1):

$$-E^1-(OA)_n-E^2-R \qquad (1)$$

wherein $E^1$ represents an alkylene containing 1 to 6 carbon atoms optionally substituted with hydroxy group or oxo group; n represents a number of 0 to 50; A independently represents an alkylene containing 1 to 6 carbon atoms, the number of A being n; $E^2$ represents ether bond or oxycarbonyl group; R represents an alkyl group containing 4 to 30 carbon atoms optionally substituted with hydroxy group, a sulfoalkyl group containing 1 to 5 carbon atoms optionally substituted with hydroxy group, or a salt thereof.

This invention also relates to a mask containing such an allergen inactivating agent and a sheet used for the mask.

This invention also relates to an allergen-inactivated cosmetic product containing such an allergen inactivating agent.

This invention also relates to a wiper sheet containing such an allergen inactivating agent.

This invention also relates to a use of the polysaccharide derivative for producing an allergen inactivating agent.

This invention also relates to a method for inactivating the allergen wherein environment of the allergen is treated with the polysaccharide derivative.

Figure 1:
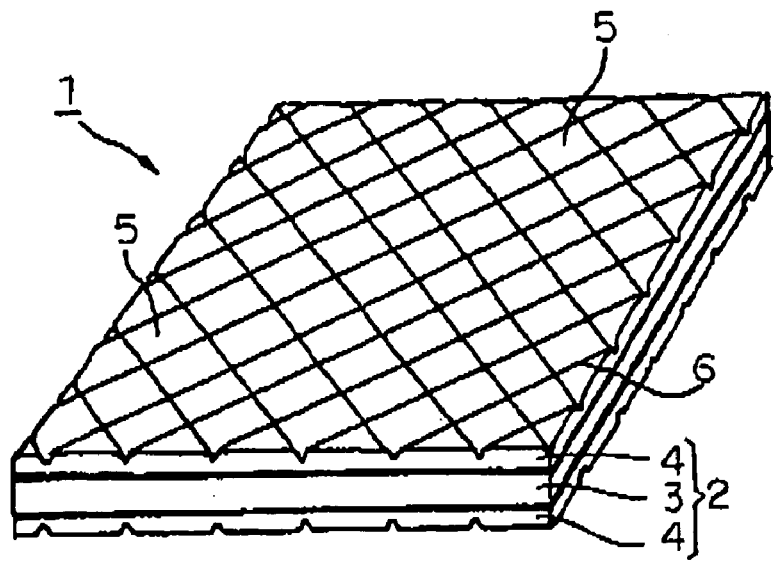
FIG. 1 is a perspective view schematically showing an embodiment of the wiper sheet of the present invention.

In the drawings, the reference numerals are used as described below.

1: floor wiper sheet, 2: sheet member, 3: interior layer, 4: exterior layer, 5: projection, 6: groove, 10: cleaner, 11: cleaning member, and 12: handle.

DETAILED DESCRIPTION OF THE INVENTION

The inventors of the present invention have conducted an extensive search for a substance which is capable of inactivating environmental allergens in a stable manner and which is also highly safe, and found that some particular polysaccharide derivatives have the action of reducing the allergic reaction-inducing capability of the allergen, and that such polysaccharide derivatives are useful as an allergen inactivating agent. Accordingly, this invention relates to an allergen inactivating agent which has no adverse effects on the human body and which is also free from the problem of the color development.

Use of the allergen inactivating agent of the present invention enables inactivation of house dust and other allergens in the environment without causing adverse effects on human body or problems such as color development.

The polysaccharide derivative of the present invention has excellent water solubility, rheological properties of increasing viscosity at a higher temperature, and excellent emulsifying action, and accordingly, it can be used as a thickener or a stabilizer in various toiletry products including viscous bath preparations, cosmetic products used in massaging, shower preparations, and skin care preparations (WO 0073351). However, it has been totally unknown that such polysaccharide derivative has the action of reducing the allergic reactions of allergen.

The polysaccharide derivative of the present invention is a polysaccharide derivative having a backbone of cellulose ether or starch ether, and preferable cellulose ether or starch ether is an alkylether wherein a part of all of the hydrogen atoms on the hydroxy group of the cellulose or the starch have been substituted.

Preferable examples of the cellulose ether include methylcellulose, ethylcellulose, hydroxymethyl cellulose, hydroxyethyl cellulose, hydroxyethyl methylcellulose, hydroxyethyl ethylcellulose, hydroxymethyl hydroxyethyl cellulose, hydroxypropyl cellulose, hydroxypropyl methylcellulose, and the most preferred include hydroxyethyl cellulose, hydroxypropyl cellulose, methyl cellulose, and hydroxypropyl methylcellulose.

Preferable examples of the starch ether include methyl starch, ethyl starch, hydroxyethyl starch, hydroxymethyl hydroxyethyl starch, and hydroxypropyl starch, and the most preferred include hydroxyethyl starch and hydroxypropyl starch.

In the cellulose ether or the starch ether as described above, hydroxy group in the hydroxyalkyl group may be further substituted with an alkyl group or a hydroxyalkyl group to form, for example, polyoxyethylene chain.

The degree of substitution by the alkyl group or the hydroxyalkyl group in the cellulose ether or the starch ether of the present invention may exceed 3.0 per constituent monosaccharide residue. The degree of substitution, however, is preferably 0.01 to 3.5, more preferably 0.1 to 3, still more preferably 1 to 3, and even more preferably 1.5 to 2. The weight average molecular weight of the cellulose ether or the starch ether of the present invention is preferably in the range of 10,000 to 2,000,000, more preferably 50,000 to 1,500,000, and yet more preferably 100,000 to 600,000.

The polysaccharide derivative of the present invention is the polysaccharide derivative wherein a part or all of the hydrogen atoms in the hydroxy group of the cellulose ether or the starch ether as described above has been replaced with a group represented by the formula (1): $-E^1-(OA)_n-E^2-R$ as shown below, and the degree of substitution is preferably 0.0001 to 1.0, more preferably 0.0005 to 0.5, still more preferably 0.001 to 0.1, and even more preferably 0.001 to 0.05 per constituent monosaccharide residue.

The polysaccharide derivative of the present invention has typical partial structure as shown below when it has hydroxyethyl cellulose for its backbone.

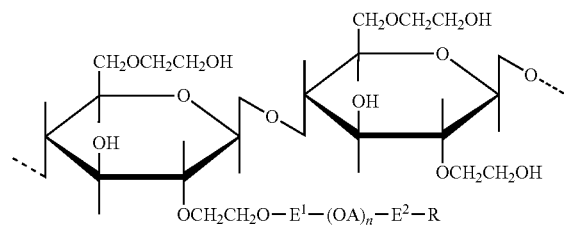

In formula (1), the alkylene group containing 1 to 6 carbon atoms optionally substituted with hydroxy group or oxo group represented by $E^1$ may be either a straight chain or a branched alkylene group, and $E^1$ is preferably a straight chain alkylene group containing 2 to 3 carbon atoms. Exemplary such alkylene groups include ethylene group, propylene group, trimethylene group, 2-hydroxytrimethylene group, 1-hydroxymethyl ethylene group, 1-oxoethylene group, 1-oxotrimethylene group, and 1-methyl-2-oxoethylene group, and the preferred are 2-hydroxytrimethylene group and 1-hydroxymethyl ethylene group.

In formula (1), the alkylene groups containing 1 to 6 carbon atoms which may be the same or different from each other represented by A may be either a straight chain or a branched alkylene group. A is preferably a straight chain alkylene group containing 2 to 3 carbon atoms. Exemplary such alkylene groups include ethylene group, propylene group, and trimethylene group, and preferred is ethylene group.

The degree of polymerization of (—OA-) represented by n is 0 to 50. The polymerization degree n, however, is preferably 0 to 40, more preferably 0 to 30, still preferably 0 to 20, still more preferably 10 to 20, and even more preferably 10 to 15 in view of inactivating the allergen. The group A which is included in the number of n may be either the same or different from each other. n is the average addition mole number.

In formula (1), $E^2$ represents ether bond or oxycarbonyl group (—OCO— or —COO—), and $E^2$ is preferably ether bond.

In formula (1), the alkyl group containing 4 to 30 carbon atoms optionally substituted with hydroxy group represented by R may be either a straight chain or a branched alkyl group. R is preferably a straight chain alkyl group containing 5 to 25 carbon atoms, more preferably the one containing 6 to 20 carbon atoms, and more preferably the one containing 6 to 20 carbon atoms. Exemplary preferable groups include octyl group, decyl group, dodecyl group, tetradecyl group, hexadecyl group, octadecyl group, and isostearyl group, and dodecyl group, hexadecyl group, and octadecyl group are preferred.

Exemplary sulfoalkyl groups containing 1 to 5 carbon atoms optionally substituted with hydroxy group represented by R include 2-sulfoethyl group, 3-sulfopropyl group, 3-sulfo-2-hydroxypropyl group, and 2-sulfo-1-(hydroxymethyl)ethyl group, and among these, the preferred are 3-sulfo-2-hydroxypropyl group and 2-sulfoethyl group.

The sulfoalkyl group may be partly or entirely in the form of a salt with an element of group I or II such as Na, K, Ca, and Mg, or an organic cation such as an amine or ammonium.

The degree of substitution of the sulfoalkyl group is preferably in the range of 0 to 1.0, more preferably 0 to 0.8, and most preferably 0 to 0.5 per constituent monosaccharide residue.

The polysaccharide derivative of the present invention can be produced in accordance with the method described in the pamphlet of WO 00/73351. In an exemplary method, the polysaccharide derivative of the present invention is produced by reacting cellulose ether or starch ether with a polyoxyalkylenating agent represented by the following general formula (2):

$$E^3-(OA)_n-E^2-R \quad (2)$$

wherein $E^3$ is an epoxidated alkyl group containing 3 to 6 carbon atoms; a halogenated alkyl group containing 1 to 6 carbon atoms which is optionally substituted with hydroxy group; or carboxy group, a carboxyalkyl group containing 2 to 6 carbon atoms, or their derivative; n, A, $E^2$, and R are as defined above, and if desired, by further reacting with a sulfonating agent (vinylsulfonic acid, a haloalkane sulfonic acid containing 1 to 5 carbon atoms which is optionally substituted with hydroxy group, a sulfonic acid containing 2 to 6 carbon atoms having epoxy group, or their salt).

The polysaccharide derivative as described above has action of reducing or eliminating antigenicity of mite allergens as will be demonstrated in the Examples. Accordingly, the polysaccharide derivative of the present invention is useful as an allergen inactivating agent which reduces or eliminates allergic reaction-inducing capability of various allergens.

The term "allergen" means a substance which causes an allergic reaction such as asthma, allergic rhinitis, pollinosis, or atopic dermatitis upon contact of a human or an animal with such substance. In the present invention, exemplary allergens include plant allergens from plant pollens of *Cryptomeria japonica, Chamaecyparis obtusa*, ragweed, orchard grass, and the like; animal allergens from epidermis, hair, and parasites of dog, cat, and other animals, insects such as cockroach and moss, mites such as *Dermatophagoides, Acarus*, and *Cryptostigmata*; fungi; bacteria; and house dusts (dust, lint, mite feces, and other house dusts).

The term "allergen inactivation" means reducing or elimination of the allergic reaction-inducing capability of the allergen itself, and with regard to animal allergens, such allergen inactivation is clearly different from the action of repellents.

More specifically, allergen inactivation can be determined as positive, for example, when allergen is measured by ELISA after treating the mite extract (protein extracted from mite) with 10 folds (weight ratio) of the agent and the quantity (ratio to the control) of Derf1 (allergen protein from mite) in relation to the control treated by distilled water is 0.8 or less, more preferably 0.7 or less, and most preferably 0.6 or less. It is to be noted that the expressions such as "covering the allergen", "blocking the allergen", "suppressing the allergen activity", "converting into a non-allergen", and "reducing the allergen" are equivalent to the allergen inactivation of the present invention.

The allergen inactivating action of the polysaccharide derivative of the present invention is particularly significant on mite allergen, house dust, ceder (*Cryptomeria japonica*) pollen allergen, and allergens of cat and other pets.

The allergen inactivating agent of the present invention can be prepared in the form of solution in oil, emulsion, wettable powder, spray, aerosol, fumigant, coating solution, detergent, powder, or particles by adding emulsifier, fixing agent, dispersing agent, wetting agent, stabilizer, propellant, or the like as desired. More specifically, the allergen inactivating agent of the present invention can be prepared into household detergent, household softener, detergent for air conditioner filter, household deodorant, reodorant, household bleach, laundry detergent, softener, laundry starch, laundry deodorant, laundry bleach, paper products for house cleaning, kitchen detergent, kitchen bleach, mask spray, or the like, and the desired effect can be realized by applying the product in various environment where allergen is present, for example, by distributing, spraying, coating, evaporating such product on floor, tatami mat, carpet, mattress, rug, tatami mat, wall, bed, sofa, pillow, or closet, by washing clothing or curtain with the product, by treating filter in the air cleaner, fabric such as mattress cover, sheets, or pillow, materials such gauze or nonwoven used in the mask, or a wiper sheet for wiping the surface of various target objects with the product.

Addition of a repellent, an insecticide, or other agents for mite, moss, cockroach, and other arthropods to the preparation as described above in addition to the polysaccharide derivative of the present invention is effective, and examples of such agents include insecticide, repellent, synergist, bacteriocide, fungicide, activating agent, deodorant, and flavoring agent for mite, moss, cockroach.

Exemplary miticides include synthetic pyrethroid such as d-phenothrin(3-phenoxybenzyl d-cis/trans-chrysanthemate), permethrin(3-phenoxybenzyl dl-cis/trans-2,2-dimethyl-3-(2',2'-dichlorovinyl)-cyclopropane carboxylate), resmethrin ((5-benzyl-3-furil)methyl dl-cis/trans-chrysanthemate), allethrin(dl-3-allyl-2-methyl-4-oxo-2-cyclopentenyl dl-cis/trans-chrysanthemate), phthalthrin((N-3,4,5,6-tetrahydrophthalimide)methyl dl-cis/trans-chrysanthemate), empenthrin(1-ethinyl-2-methyl-2-pentenyl dl-cis/trans-chrysanthemate), and d,dT80-pralethrin(d-2-methyl-4-oxo-3-propargylcyclopent-2-enyl d-cis/trans-chrysanthemate) and their derivatives, and anti-mite reagents derived from a natural essential oil such as hinokitiol, benzyl benzoate, and jasmonic acid derivative.

Exemplary mite repellents that may be used include diethylamide, dimethyl phthalate, dibutylphthalate, MGK repellent 326, dubtlex, 2-ethyl-1,3-hexanediol.

Exemplary miticide synergist and/or miticide include piperonyl butoxide, octachlorodipropylether, N-(2-ethylhexyl)-1-isopropyl-4-methylbicyclo[2,2,2]octo-5-en-2,3-dicarboxyimide, and N-(2-ethinyl)-bicyclo[2,2,1]-hepta-5-en-2,3-dicarboxyimide.

Examples of bacteriocide and fungicide which suppress proliferation of the fungi or the bacteria having antigenicity by itself and serving food for the house dust mites include tiabendazole, triclosan, chlorhexidine, zinc pyrithione, chloroxylenol, densil, benzalkonium chloride, dichlofluanid, sodium benzoate, p-methyl oxybenzoate, phenoxy ethanol, and ethanol, as well as natural components such as chitosan, catechin, thymol, hinokitiol, Phyllostachys extract, mustard essential oil, and wasabi essential oil.

The preparation as described above may contain the polysaccharide derivative of the present invention in combination with a known anti-allergen reagent such as tannic acid, tea extract, hydroxyapatite, epicatechin, epigallocatechin gallate, epigallocatechin gallate, or gallic acid (Japanese Patent Application Laid-Open No. 6-279273); smectite or other clay mineral which is an allergen catching reagent; or a hydroxybenzoate compound which is known to be an allergen removing agent (Japanese Patent Application Laid-Open No. 11-292714).

A mask and other products having the allergy preventing effect may be produced by spraying or impregnating the allergen inactivating agent of the present invention to a mask or a sheet used therefor such as gauze or nonwoven. The preparation used for the spraying or impregnation is preferably a mixture based on water or alcohol, and the alcohol is preferably ethanol, propanol, isopropanol, or 1,3-butylene glycol.

The sheet material used for constituting the mask (sheet for the mask) may be any material as long as it is air permeable, and the sheet material may be, for example, a woven fabric such as gauze, a nonwoven, or a paper (such as pulp paper or rayon fiber paper). Preferable materials include dry nonwovens such as thermally bonded nonwoven, spunlace nonwoven, and chemical bond nonwoven and wet nonwovens such as spunbond nonwoven, and meltblown nonwoven. The fiber constituting the nonwoven may be a thermoplastic fiber such as polyester fiber, polyamide fiber, or polyolefin fiber; their complex fiber or split fiber; a semi-synthetic fiber such as acetate; a regenerated fiber such as cupura or rayon; a natural fiber such as cotton or pulp; a mixture thereof, and the type of the fiber used may be adequately selected depending on the production method.

Such sheet for the mask may be fabricated into the mask product by attaching ear hangers to the sheet, by forming ear hanger holes in the sheet material itself, or by inserting the sheet as an auxiliary sheet between the mask and the mouth (on the surface or in the interior of the mask or at the part of the mask that corresponds to the mouth).

In such a case, the polysaccharide derivative is preferably incorporated in the allergen inactivating agent at an amount of 0.001 to 30% by weight, and preferably at 0.01 to 5% by weight, and the amount of the allergen inactivating agent impregnated in the sheet is preferably 0.01 to 60 folds, and more preferably 0.1 to 10 folds of the sheet weight.

Conventional masks for pollinosis are associated with the risk that symptoms of allergic diseases may be induced when the pollen, mite, or other allergen that had been caught by the mask is released from the mask and inhaled by the patient. In contrast, the mask and the sheet for the mask of the present invention have the merit that such allergic symptoms are less likely to be induced even if the allergen that had been caught were released from the mask since the caught allergen is detoxicated as soon as it is caught by the mask.

The allergen inactivating agent of the present invention may also be used in producing a wiper sheet by spraying or impregnating the allergen inactivating agent to a sheet member of nonwoven or the like, and the wiper sheet may be used to reduce the allergen on the surface of the object which is wiped by the sheet. Next, the wiper sheet of the present invention is described by referring to an embodiment which is adapted for use in cleaning the floor.

As shown in FIG. 1, the wiper sheet 1 contains a sheet member 2 having impregnated therein an allergen inactivating agent. More specifically, the wiper sheet is a wet wiper sheet wherein a sheet member 2 is impregnated with an aqueous detergent containing a polysaccharide derivative substituted with the group represented by general formula (1) of the present invention to thereby produce a wet wiper sheet wherein the allergen reducing agent is impregnated with the sheet member 2.

The sheet member 2 is a laminate of interior layer 3 and a pair of exterior layers 4 sandwiching the interior layer 3.

The sheet member is preferably impregnated with the aqueous detergent containing the polysaccharide derivative at an amount of 100 to 1000% by weight in relation to the weight of the sheet member (namely, based on the weight of the wiper sheet before the impregnation (in the dry state)). When the amount of impregnation is less than 100% by weight, the sheet will exhibit insufficient cleaning performance for the dirt and the dust. When the amount of impregnation is in excess of 1000% by weight, too much detergent will be released onto the floor with the dirt and the dust remaining on the floor, and such excessive amount of detergent may adversely affect some wood based floors. In order to improve the cleaning performance, the aqueous detergent is impregnated preferably at an amount of 150 to 350% by weight, and more preferably at an amount of 200 to 300% by weight. The amount of the aqueous detergent impregnated in the sheet member may be determined by weighing the impregnated sheet with no load either with or without mangling treatment to remove the excessive aqueous detergent, and comparing the thus measured weight in relation to the weight of the sheet member itself.

The sheet member 2 (namely, the wiper sheet 1 before the impregnation with the aqueous detergent containing the polysaccharide derivative) preferably has a grammage of 40 to 200 g/m². When the grammage of the sheet member is less than 40 g/m², impregnation of the detergent required for wiping the floor of large area will be difficult. When the grammage is in excess of 200 g/m², the increased weight may adversely affect the handling properties, and the cost will be increased. The grammage is preferably in the range of 50 to 150 g/m², and more preferably 55 to 100 g/m². The sheet member may preferably have a thickness of 0.2 to 10 mm in dry state and under the load of 3 g/m², and in view of the trackability of the member with the irregular surface of the floor and the cost, the thickness is preferably in the range of 0.4 to 5 mm, and more preferably 0.6 to 2 mm.

The exterior layers 4 of the sheet member 2 constitute the surface layers of the wiper sheet 1 of this embodiment, and the surface is the part that becomes in contact with the floor in the use of the wiper sheet 1. In view of providing a sufficient surfecestrength to the surface of the wiper sheet 1, the exterior layer 4 preferably contains a nonwoven containing fibers having a fiber length of at least 20 mm, more preferably 30 to 100 mm, and even more preferably 35 to 65 mm. The nonwoven containing the fiber with the fiber length of at least 20 mm does not necessarily require that every fiber constituting the nonwoven has the length of at least 20 mm, and the inclusion of the fiber with the fiber length of less than 20 mm that is inevitably included and/or generated in the starting material and/or in the process of the nonwoven is admitted. While the exterior layer 4 corresponds to the surface layer in this embodiment, the surface layer of the sheet may designate the surface and the neighboring area of the sheet when the sheet to be impregnated with the detergent is the one having a monolayer structure.

As shown in FIG. 1, the sheet member 2 is thermally embossed in diagonal lattice pattern, and the surface has a large number of projections 5 and linear grooves 6 defining the projections 5 formed by the embossing. The density of the area of the groove 6 is higher than the area of the projection 5 due to the heat and pressure applied during the thermal embossing process. The area constituted by the projection 5 is preferably 30 to 95%, more preferably 40 to 85%, and most preferably 50 to 80% in relation to the apparent area of the cleaning surface of the wiper sheet 1 in view of simultaneously attaining the catching performance of the hair and lint and handling convenience of the cleaner in the cleaning. The apparent area of the cleaning surface of the wiper sheet 1 means the area of the cleaning area when the wiper sheet 1 is regarded to contain a flat plane.

The area of the projection 5 is measured by placing a piece of wiper sheet (10 cm×10 cm) impregnated with the predetermined amount of aqueous detergent on a special paper used for practicing calligraphy (KN37-10 manufactured by Kuretake-Seikado) wherein the color of the part wetted by water darkens to black; applying a load by placing a 10×10 cm acrylic plate (25 g) and a weight of 2000 g for 60 seconds, and promptly removing the weight and the acrylic plate; measuring the area that turned black in the calligraphy paper using an image analyzer (New Qube, manufactured by Nexus) to use the measured area as the area of the projection 5. The area of the projections 5 was then divided by 100 cm² (the apparent area of the cleaning surface of the wiper sheet) to calculate the proportion of the area of the projection 5.

The pattern of the groove 6 formed by the embossing as described above is not limited to the one shown in FIG. 1. The pattern, however, is preferably the one having continuous straight and/or curved line in one part. In view of retaining surfecestrength of the wiper sheet 1, the pattern preferably contains continuous linear grooves 6 and projections 5 surrounded by the grooves 6. When the groove 6 contains a straight or curved line, the groove may preferably have a width of 0.5 to 3 mm. The distance between the grooves 6 may be adequately adjusted by the property required for the wiper sheet 1. Use of the combination of the pattern of continuous lines as described above with the pattern of non-continuous spots is also preferable.

As described above, the exterior layer 4 of the sheet member 2 may preferably contain a nonwoven. The nonwoven is preferably a spunlace nonwoven which can realize loose intertwining of the fiber in view of the sheet texture and the ability to catch the hair and lint by the intertwining with the sheet.

The fibers constituting the exterior layer 4 may preferably contain hydrophilic cellulose fiber and low melting thermoplastic fiber in order to maintain cleaning performance, handling convenience, and sheet strength.

The hydrophilic cellulose fiber may preferably comprise 30 to 98% by weight, and more preferably 50 to 90% by weight of the exterior layer 4 for efficient removal of the dirt and the dust since hydrophilic cellulose fibers are excellent in absorbing the solution having the dirt and dust dissolved or dispersed therein. Exemplary hydrophilic cellulose fibers include rayon and cotton fibers.

The low melting thermoplastic fiber may preferably comprise 2 to 70% by weight, and more preferably, 10 to 50% by weight of the exterior layer 4 for improving strength of the sheet after the thermal embossing as well as excellence of the handling convenience.

The low melting thermoplastic fiber is preferably the one having a melting point of up to 200° C., and more preferably, the one having a melting point of up to 170° C. Typical such fibers include polyethylene fiber, polypropylene fiber, low melting polyethylene terephthalate fiber, polyvinyl alcohol fiber, and a core-shell fiber of these fibers wherein the shell component has the lower melting point and the core component has the higher melting point, and a side-by-side fiber of these fibers containing the fiber of lower melting point and the fiber of higher melting point.

In order to improve cleaning performance, handling convenience, and sheet texture, the exterior layer 4 may also contain a synthetic fiber in addition to the hydrophilic cellulose fiber and the low melting thermoplastic fiber. Exemplary such additional synthetic fibers include polyester fiber, polyacrylonitrile fiber, Nylon fiber, acetate fiber, polyvinyl alcohol fiber, and polyvinyl chloride fiber.

The fibers constituting the exterior layer 4 is not particularly limited for the fiber diameter. The fiber, however, preferably has a diameter of up to 3.3 dtex, and use of the fiber having a diameter of 0.5 to 2.0 dtex is more preferable in view of the higher ability of catching hair and lint. In addition, the fiber is not particularly limited for its length, and the fiber may be either a long filament or a short staple fiber.

The exterior layer 4 may preferably have a grammage of 8 to 70 g/m$^2$, and more preferably 15 to 30 g/m$^2$ in consideration of the grammage of the sheet member as described above. The thickness of the exterior layer 4 (namely, the thickness of each exterior 4) is preferably 0.05 to 5 mm, and in view of the hair and lint catching ability and the cost, the thickness is preferably in the range of 0.1 to 2 mm, and more preferably 0.2 to 1 mm.

The interior layer 3 constituting the sheet member may contain a sheet material such as paper, nonwoven, woven fabric, or resin net, and this sheet material may preferably have a breaking strength of at least 200 cN/25 mm in consideration of retaining strength of the wiper sheet. When the sheet member has a grammage of up to 100 g/m$^2$, the interior layer 3 preferably contains a bulky sheet material with low density in order to retain aqueous detergent and provide strength, thick texture, and cushioning property with the sheet member. Exemplary materials used for the interior layer 3 having such properties include nonwovens such as thermal bond (air through) nonwoven, spunlace nonwoven, and air laid nonwoven. Although higher breaking strength is preferable as described above, the upper limit of the breaking strength in practical point of view is approximately 100 N/25 mm.

When the interior layer 3 is constituted form fibers, the fiber used may be a hydrophilic fiber such as rayon, cotton, pulp, or polyvinyl alcohol fiber. Use of a hydrophobic fiber as main component is also preferable in consideration of increasing the thickness of the interior layer 3 and improving the cushioning property. Exemplary such hydrophobic fibers include polyolefin fibers such as polyethylene and polypropylene, polyamide fibers such as Nylon and polyester, polyacrylonitrile fiber, as well as core/shell fibers and side-by-side fibers thereof. In order to increase the thickness and the cushioning property of the interior layer 3, the fibers is preferably provided with 3D crimps. When grooves and projections are to be provided on the surface of the sheet member 2 by conducting a heat treatment, the fiber used is preferably a heat-shrinkable fiber or a heat crimping fiber.

When the interior layer 3 is constituted form fibers, the fiber used is not particularly limited for the fiber diameter. The fiber diameter, however, is preferably in the range of 1 to 7 dtex in order to increase the thickness and cushioning property. In addition, the fiber is not limited for its length, and the fiber may be either a long filament or a short staple fiber.

The interior layer 3 may preferably have a grammage of 20 to 150 g/m$^2$, and more preferably 25 to 80 g/m$^2$ in consideration of the grammage of the sheet member as described above. The thickness of the interior layer 3 is preferably 0.2 to 4.8 mm, and in order to realize the thickness and the cushioning property as well as the low cost that allows use of the product as a disposable product with no hesitation, the thickness is preferably in the range of 0.4 to 3 mm, and more preferably 0.6 to 2 mm.

When a resin net is used for the interior layer, the interior layer may preferably have a grammage of 3 to 150 g/m$^2$, and more preferably 5 to 50 g/m$^2$. In this case, the grammage of the exterior layer is correspondingly increased as desired. In addition, the amount of the hydrophilic cellulose fiber in the exterior layer is preferably reduced in this case in consideration of the handling convenience and the amount of the detergent released on the floor, and the hydrophilic cellulose fiber is preferably incorporated at 10 to 80% by weight, and more preferably, at 20 to 60% by weight of the exterior layer. The thermoplastic fiber may not be necessarily incorporated since thermal embossing is not required due to the sufficient strength realized by the spunlace process, and the thermoplastic fiber and the synthetic fiber may be incorporated at a combined amount of 20 to 90% by weight, and more preferably, at 40 to 80% by weight of the exterior layer.

The sheet member 2 containing the interior layer 3 and the exterior layer 4 as described above may be produced, for example, by first producing a spunlace nonwoven for the exterior layer 4 wherein the fibers are loosely intertwined with high degree of freeness; separately producing a thermally bonded nonwoven for the interior layer 3 which is bulky with low density; disposing the exterior layer 4 on each side of the interior layer 3; and thermally embossing the resulting laminate for integration of the three layers to thereby form the sheet member.

In another preferable method, fiber webs prepared by carding are placed on both sides of a thermally bonded nonwoven corresponding to the resulting interior layer 3, and the fibers are intertwined by using a water jet (water needling) to intertwine the fibers of the webs with the spunlace nonwoven constituting the exterior layer 4, and simultaneously, to intertwine fiber webs with the interior layer 3 containing the thermally bonded nonwoven to thereby produce a complex spunlace nonwoven containing loosely intertwined fibers. The resulting nonwoven contains the thermally bonded nonwoven which is a sheet material, and the nonwoven-like fiber assemblies (spunlace nonwovens) formed by the intertwining of the fibers of the fiber webs sandwiching the thermally bonded nonwoven, and the resulting nonwoven are integrated by both the intertwining of the fibers of the spunlace nonwovens and the intertwining of the fibers of the spunlace nonwovens with the fibers of the thermally bonded nonwoven. This nonwoven is then thermally embossed to form the sheet member.

Irrespective of the method used for the production, in consideration of efficient catching of the hair and lint, the fibers constituting the surface layer that becomes in contact with the floor in the use may preferably have a high degree of freedom, and in other words, the surface layers may preferably have loose intertwining of the fibers.

Figure 3:
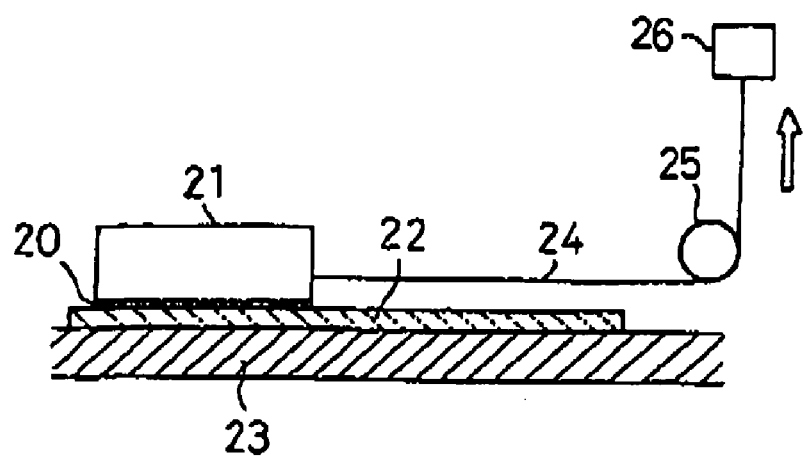
FIG. 3 is a schematic view showing the procedure of measuring static frictional resistance value of the wiper sheet.

Static frictional resistance value may be employed as an index for the fiber intertwining in the surface layer of the wiper sheet 1 of this embodiment. The static frictional resistance value is measured by the method shown in FIG. 3. A sand paper (waterproof sandpaper Techno Sander manufactured by 3M, 1200 grit) 20 is attached to the bottom surface (10 cm×10 cm) of a weight 21 (having a total weight of 400 g including the sand paper), and this weight is placed on a wiper sheet 22 (200 mm×280 mm) impregnated with an aqueous detergent which is firmly secured on a horizontal table 23 so that the sand paper side of the weight feces the wiper sheet. A thread 24 is attached to the side surface of the weight, and the other end of the thread 24 is connected to a load cell 26 of a tensile tester (RTM-25 manufactured by Orientech) with a pulley 25 placed in between. The tensile tester is started and the weight 21 is moved 30 mm in horizontal direction at a speed of 500 mm/min to thereby measure initial maximum static frictional resistance value. This value is used for the index of the degree fiber intertwining. The value is measured for both the machine direction (MD) and the cross direction (CD) of the wiper sheet which had been determined in the production process of the sheet. New sand paper is used in every measurement.

In the surface layer of the wiper sheet impregnated with the aqueous detergent, the static frictional resistance value is likely to become increased with the increase in the looseness of the fiber intertwining, namely, with the increase in the fiber freedom, since fibers are more likely to be caught by the sandpaper when they are loosely intertwined.

The static frictional resistance value which is an index for the fiber intertwining of the surface layer in the wiper sheet 1 is preferably in the range of 900 to 2500 cN. When the static frictional resistance value is less than 900 cN, ability to catch hair and lint will be insufficient. On the other hand, the static frictional resistance value in excess of 2500 cN will result in the insufficient surfecestrength of the sheet, and the fiber will be caught by the burrs and other projections of the floor and smooth handling of the mop may become difficult. The static frictional resistance value is more preferably in the range of 1100 to 2200 cN, and even more preferably in the range of 1200 to 2000 cN. It is certainly preferable that the wiper sheet 1 has the static frictional resistance value within such range when measured in both the MD and the CD. However, it is sufficient if the wiper sheet 1 has the value within such range when measured in either direction.

The sheet member 2 may preferably have a breaking strength of at least 200 cN/25 mm, and more preferably at least 300 to 8000 cN/25 mm in consideration of simultaneously reducing the detachment of fibers from the surface layer and improving the ability to catch the hair and lint. The breaking strength of the sheet member should be within such range at least when measured in either the machine direction (MD) or the cross direction (CD).

The aqueous detergent may preferably contain water as the medium together with the polysaccharide derivative of the present invention, a surfactant, an alkaline chemical, a thickener, and an aqueous solvent. Preferably, all the components incorporated in the aqueous detergent are substantially water-soluble. Amount of the involatile component which remains after the volatilization is preferably up to 10% by weight, more preferably up to 5% by weight, even more preferably up to 1% by weight, in consideration of the finishing after the cleaning.

The polysaccharide derivative is preferably incorporated in the aqueous detergent at a total amount of 0.005 to 2% by weight, more preferably at 0.01 to 1% by weight, and even more preferably at 0.05 to 0.5% by weight in order to reduce the amount of the allergen and improve cleaning ability and finishing of the surface cleaned.

The surfactant used may be either an anionic surfactant, a nonionic surfactant, a cationic surfactant, or an amphoteric surfactant. In order to simultaneously realize sufficient cleaning ability and finishing, the surfactant is preferably a nonionic surfactant such as polyoxyalkylene (mole number of alkylene oxide added, 1 to 20), alkyl($C_{8-22}$ straight chain or branched alkyl)ether, alkyl($C_{8-22}$ straight chain or branched alkyl)glycoside (average degree of sugar condensation 1 to 5), sorbitan fatty acid ($C_{8-22}$ straight chain or branched)ester, or alkyl(straight chain or branched $C_{6-22}$)glyceryl ether; or a $C_{8-24}$ amphoteric surfactant such as alkylcarboxybetaine, alkylsulfobetaine, alkylhydroxysulfobetaine, alkylamidocarboxybetaine, alkylamidosulfobetaine, or alkyllamidohydroxysulfobetaine. The surfactant is preferably incorporated in the aqueous detergent at an amount of 0.01 to 1.0% by weight, and most preferably 0.05 to 0.5% by weight in consideration of the cleaning ability and finishing of the surface cleaned.

Examples of the preferable alkaline chemicals include a hydroxide such as sodium hydroxide; a carbonate such as sodium carbonate; an alkaline sulfate such as sodium hydrogensulfate; a phosphate such as monobasic sodium phosphate; organic alkaline metal salt such as sodium acetate and sodium succinate; an alkanolamine such as ammonia, mono, di, and triethanolamine; β-aminoalkanol such as 2-amino-2-methyl-1-propanol; and morpholine. The most preferred is an alkanolamine such as mono, di, or triethanolamine; a β-aminoalkanol such as 2-amino-2-methyl-1-propanol, or morpholine in view of the texture and pH buffering ability. The alkaline chemical is preferably incorporated in the aqueous detergent at 0.01 to 1% by weight, and most preferably, at 0.05 to 0.5% by weight in consideration of the cleaning ability and texture.

Exemplary thickeners include water soluble polymers such as natural polysaccharide, cellulose polymer, starch polymer and other semisynthetic polymers, vinyl polymer, polyethylene oxide, and other synthetic polymers, and clay minerals. Use of a polyacrylic thickener, an alkyl acrylate-alkyl methacrylate copolymer thickener, or a mixture thereof is preferable in view of the low tackiness and less slippery texture. The acrylic thickener is preferably the one which becomes viscous in the state of sodium salt. The thickener is preferably incorporated in the aqueous detergent at an amount of 0.01 to 2% by weight, and more preferably, at 0.02 to 1% by weight in view of the finishing of the cleaned surface.

The aqueous solvent is preferably at least one solvent selected from monohydric alcohol, polyhydric alcohol, and derivatives thereof. In consideration of the finishing quality, use of an aqueous solvent having a vapor pressure of at least 267 Pa (2 mmHg) is preferable. Examples include ethanol, isopropyl alcohol, propanol, ethylene glycol monomethyl ether, and propylene glycol monomethyl ether. In order to reduce odor and skin irritation, the content of the aqueous solvent in the aqueous detergent is preferably 1 to 50% by weight, and more preferably 1 to 20% by weight.

The aqueous detergent may contain the polysaccharide derivative of the present invention in combination with an adequate amount of substance known as an anti-allergen reagent such as tannic acid, tea extract, hydroxyapatite, epicatechin, epigallocatechin gallate, epigallocatechin gallate, and gallic acid (Japanese Patent Application Laid-Open No. 6-279273), a clay mineral such as smectite which is an allergen capturing substance, hydroxybenzoate compound which is known as an allergen-removing agent (Japanese Patent Application Laid-Open No. 11-292714), and the like.

The aqueous detergent may also include a sterilizer in addition to the components as described above so that the resulting aqueous detergent may have sterilizing effect in addition to the cleaning effect. Exemplary preferable sterilizers include hydrogen peroxide, hypochlorous acid, sodium hypochlorite, quaternary ammonium salt, sodium benzoate, sodium paraoxybenzoate, polylysine, and other natural stabilizers, and use of quaternary ammonium salt, polylysine, and other natural sterilizer is preferable in view of the stability after the blending as well as the sterilization performance. The sterilizer is preferably incorporated in the aqueous detergent at an amount of 0.005 to 2% by weight, and more preferably, at 0.01 to 1% by weight in order to realize a good balance between the sterilization effect and decrease in the skin irritation.

The aqueous detergent may preferably contain water as its medium preferably at a content of 50 to 99.9% by weight, and more preferably at 80 to 99% by weight in view of the finishing quality of the cleaned surface.

The sheet member 2 is impregnated with the aqueous detergent to form the wiper sheet 1 of this embodiment, and the wiper sheet 1 is thereby provided with the properties of a wet sheet. The aqueous detergent is the one having a viscosity of 20 to 30000 mPa·s at 25° C. Use of the aqueous detergent with the viscosity of such range has the merits including: (1) amount of the aqueous detergent released at the beginning of the cleaning will be reduced so that the amount of the aqueous detergent released will be consistent from the start to the end of the cleaning, (2) cleaning ability will be retained in the case of cleaning a large area, (3) the value of the frictional resistance of the wiper sheet against the floor will be reduced since amount of the aqueous detergent released at the beginning of the cleaning is reduced, and (4) fibers at the surface of the wiper sheet enjoy high freedom since amount of the aqueous detergent released at the beginning of the cleaning is reduced, and thus the sheet is capable of catching and retaining the hair and the lint. When the viscosity of the aqueous detergent is less than 20 mPa·s, it will be difficult to reduce the amount of aqueous detergent released onto the floor at the beginning of the cleaning. When the viscosity is in excess of 30000 Pa·s, impregnation of the aqueous detergent in the sheet member will be difficult. In order to reduce the amount of aqueous detergent released at the beginning of the aqueous detergent and improve handling convenience in the impregnation of the aqueous detergent to the sheet member, the viscosity is preferably in the range of 100 to 1000 mPa·s, and more preferably, 300 to 800 mPa·s.

The viscosity is measured by using Brookfield viscometer, and the rotor and the revolution number used are adequately determined depending on the viscosity of the aqueous detergent.

Preferably, the aqueous detergent is substantially free from water-insoluble solid particles. When the water-insoluble solid particles are incorporated in the aqueous detergent, the solid particles will remain on the surface cleaned and the surface need to be wiped again. However, the aqueous detergent may contain a minute amount of such solid particles, for example, at a content of up to 0.1% by weight as impurities.

Figure 2:
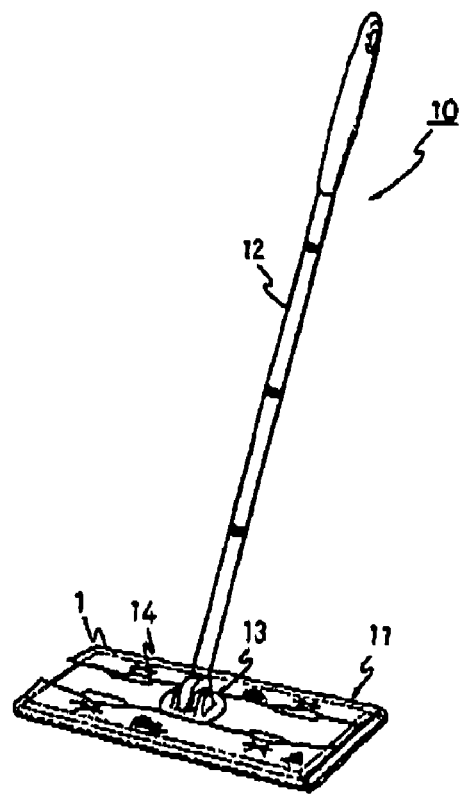
FIG. 2 is a perspective view showing the wiper sheet of the present invention attached to the cleaner.

The wiper sheet 1 of this embodiment is used with a cleaner 10 as shown in FIG. 2 containing a cleaning member 11 and a rod handle 12 connected to the cleaning member 11, and the wiper sheet 1 is mounted on the cleaning member 11. More specifically, the cleaner 10 contains the cleaning member 11 which is flat and on which the wiper sheet 1 can be mounted, and the rod handle 12 connected to the cleaning member 11 by the intervening universal joint 13. The wiper sheet 1 is secured between the radial slits formed by a plurality of flexible tabs 14 provided on the cleaning member 11.

The wiper sheet of this embodiment enables stable and gradual release of the detergent as well as easy handling, and cleaning of a large area of the floor is thereby enabled.

The present invention is not limited to the embodiment as described above. While the wiper sheet 1 of this embodiment has the three layer structure having a polysaccharide derivative-containing aqueous detergent impregnated therein, the sheet member may be substituted with the one having a sheet of single layer, double layer, or four layer structure. For example, the exterior layer 3 may be disposed in the embodiment as described above only on one side of the interior layer 2, and the pattern of the projections and the grooves on the surface of the wiper sheet 1 in the embodiment as described above may also be varied for the ease of the production or handling convenience of the wiper sheet 1.

The object wiped by the wiper sheet of the present invention is not limited. In addition to the floor as in the case of the embodiment as described above, the wiper sheet may be used for wiping, for example, surface of structural materials such as wall, ceiling, and pole of a building, furniture such as table and sofa, home-appliance such as TV, kitchen utilities, OA equipment such as personal computer, clothing, bedding, and commodities such as bags and packs. The wiper sheet may be used also for wiping human body, pets and other animals, ornamental plants, and everything where allergen may become attached.

Alternatively, the allergen inactivating agent of the present invention may be directly applied to the skin as an external agent as in the case of cosmetic product, for example, in the form of water-in-oil or oil-in-water cosmetic emulsion, cream, gel, cosmetic emulsion, lotion, oily cosmetic product, facial wash, foundation, pack, cataplasm, spray, mist, lip stick, hairtonic, hairdressing, shampoo, hair rinse, hair conditioner, and other skin detergent.

Such cosmetic product may be formulated by combining the allergen inactivating agent with any desired components commonly used in the cosmetic products such as oil content, ceramide, pseudoceramide, sterol, moistening agent, antioxidant, singlet enzyme quencher, powder component, colorant, UV absorber, whitening agent, alcohols, chelating agent, pH adjusting agent, preservative, thickener, pigment, flavor, plant extract, various skin nutrients.

Amount of the polysaccharide derivative of the present invention incorporated in the preparation as described above may be adequately determined depending on the dosage form, the treatment method, and the site of the treatment. The polysaccharide derivative, however, is preferably incorporated at 0.001 to 20% by weight, and more preferably at 0.01 to 10% by weight of the entire composition. When the preparation is used with no further dilution, the amount incorporated is preferably in the range of 0.01 to 2% by weight, and when the preparation is used after dilution, the polysaccharide derivative is preferably incorporated so that the amount is 0.1 to 10% by weight in the stock solution, and the stock solution is preferably diluted to 10 to 10,000 fold before its use.

When the allergen inactivating agent of the present invention is used for external agent applied on the skin as in the case of cosmetic product, the allergen inactivating agent is preferably incorporated in the product at an amount of 0.001 to 20% by weight, and more preferably at 0.01 to 10% by weight.

EXAMPLES

Next, the present invention is described in further detail by referring to the Examples.

Production Example 1

80 g of hydroxyethyl cellulose (HEC-QP100MH manufactured by Union Carbide Company) having a weight average molecular weight of 1,500,000 and degree of substitution by hydroxyethyl group of 1.8, 640 g of 80%

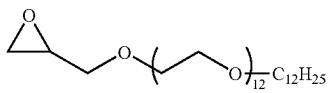

isopropyl alcohol, and 5.34 g of 48% aqueous solution of sodium hydroxide were mixed to produce a slurry, and the slurry was stirred in nitrogen atmosphere at room temperature for 30 minutes. To this solution was added 12.78 g of polyoxyalkylenating agent represented by the following formula:

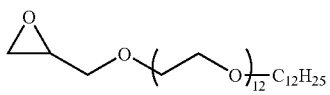

and the mixture was allowed to react at 80° C. for 8 hours for polyoxyalkylenation. After the termination of the reaction, the reaction solution was neutralized with acetic acid, and the reaction product was separated by filtration. The reaction product was washed twice with 500 g of isopropyl alcohol, and dried under reduced pressure at 60° C. for one day to produce 72.0 g of polyoxyalkylenated hydroxyethyl cellulose derivative (Compound 1).

The degree of substitution of the substituent containing the polyoxyalkylene group in the resulting hydroxyethyl cellulose derivative was 0.004.

Production Example 2

Compounds 2 to 16 shown in Table 1 were produced by the methods described in Production Example 1 and in WO 00/73351.

Production Example 3

(1) To a 1000 mL glass separable reaction vessel equipped with agitator, thermometer, and condenser were added 80 g of hydroxyethyl cellulose (HEC-QP100M manufactured by Union Carbide Company) having a weight average molecular weight of about 1,500,000 and degree of substitution by hydroxyethyl group of 1.8, 640 g of 80% isopropyl alcohol, and 5.5 g of 48% aqueous solution of sodium hydroxide to prepare a slurry, and the slurry was stirred in nitrogen atmosphere at room temperature for 30 minutes. To this solution was added 2.52 g of stearyl glycidylether, and the mixture was allowed to react at 80° C. for 8 hours for hydrophobicization. After the termination of the hydrophobicization reaction, the reaction solution was neutralized with acetic acid, and the reaction product was separated by filtration. The reaction product was washed twice with 500 g of isopropyl alcohol at 50° C., and then, twice with 500 g of acetone, and dried under reduced pressure at 70° C. for one day to produce 72.8 g of hydrophobicized hydroxyethyl cellulose derivative.

(2) To a 500 mL glass separable reaction vessel equipped with agitator, thermometer, and condenser were added 20.0 g of hydrophobicized hydroxyethyl cellulose derivative produced in (1), 200 g of 70% isopropyl alcohol, and 1.37 g of 48% aqueous solution of sodium hydroxide to produce a slurry, and the slurry was stirred in nitrogen stream at room temperature for 30 minutes. To the reaction solution were added 28 g of sodium 3-chloro-2-hydroxypropane sulfonate and 11.9 g of 48% aqueous solution of sodium hydroxide, and sulfonation was allowed to proceed at 50° C. for 3 hours. After the termination of the reaction, the reaction solution was neutralized with hydrochloric acid and the reaction product was separated by filtration. The reaction product was washed once with 340 g of 70% isopropyl alcohol, and then twice with 120 g of isopropyl alcohol, dried under reduced pressure at 70° C. for 1 day to produce 18.3 g of hydroxyethyl cellulose derivative substituted with 3-stearyloxy-2-hydroxypropyl group and 3-sulfo-2-hydroxypropyl group (Compound 17).

The resulting hydroxyethyl cellulose derivative had a degree of substitution by 3-stearyloxy-2-hydroxypropyl group of 0.003, and a degree of substitution by 3-sulfo-2-hydroxypropyl group of 0.210.

Production Example 4

Compound 18 shown in Table 1 was produced by the method of Production Example 3.

Production Example 5

80 g of hydroxyethyl cellulose (HEC-QP15000H manufactured by Union Carbide Company) having a weight average molecular weight of about 800,000 and degree of substitution by hydroxyethyl group of 1.8, 640 g of 80% isopropyl alcohol, and 2.0 g of p-toluenesulfonic acid were mixed to produce a slurry, and the slurry was stirred in nitrogen atmosphere at room temperature for 30 minutes. To this solution was added 15 g of the compound represented by the following formula:

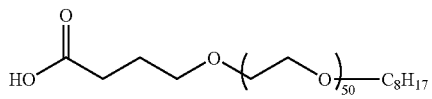

and the mixture was allowed to react at 80° C. for 8 hours for polyoxyalkylenation. After the termination of the reaction, the reaction solution was neutralized with 48% aqueous solution of sodium hydroxide, and the reaction product was separated by filtration. The reaction product was washed twice with 500 g of isopropyl alcohol, then twice with 500 g of isopropyl alcohol, and dried under reduced pressure at 70° C. for one day to produce 73.4 g of polyoxyalkylenated hydroxyethyl cellulose derivative (Compound 19).

The degree of substitution of the substituent containing the polyoxyalkylene group in the resulting hydroxyethyl cellulose derivative was 0.010.

Production Example 6

(1) 80 g of potato starch (manufactured by Katayama Chemical, Inc.), 640 g of 50% isopropyl alcohol, and 5.5 g of 48% aqueous solution of sodium hydroxide were mixed to produce a slurry, and the slurry was stirred in nitrogen atmosphere at room temperature for 30 minutes. To this solution was added 19.0 g of compound represented by the following formula:

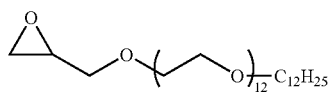

and the mixture was allowed to react at 80° C. for 8 hours for polyoxyalkylenation. After the termination of the reaction, the reaction solution was neutralized with acetic acid, and the reaction product was separated by filtration. The reaction product was washed twice with 500 g of 50% isopropyl alcohol, and dried under reduced pressure at 70° C. for one day to produce 69.4 g of polyoxyalkylenated starch derivative.

The degree of substitution of the substituent containing the polyoxyalkylene group in the resulting starch derivative was 0.005.

(2) 35.5 g of the polyoxyalkylenated starch produced in (1), 350 g of 70% isopropyl alcohol, and 2.4 g of 48% aqueous solution of sodium hydroxide were mixed to produce a slurry, and the slurry was stirred in nitrogen atmosphere at room temperature for 30 minutes. To the reaction solution were added 25.1 g of sodium monochloroacetate and 18.0 g of 48% aqueous solution of sodium hydroxide, and carboxymethylation was allowed to take place at 50° C. for 5 hours. After the termination of the reaction, the reaction solution was neutralized with acetic acid, and the resulting product was separated by filtration. The resulting product was washed three times with 400 g of 70% isopropyl alcohol, then twice with 300 g of isopropyl alcohol, and dried under reduced pressure at 70° C. for 1 day to produce 33.8 g of starch derivative which had been polyoxyalkylenated and carboxymethylated (Compound 20). The resulting starch derivative had degree of carboxymethylation of 0.48.

TABLE 1

| | | Backbone (Cellulose ether or starch ether) | | | Substituent [-$E^1$-(OA)$_n$$E^2$-R—] | | | | | |
|---|---|---|---|---|---|---|---|---|---|---|
| Compound | Code number | Substance | Average molecular weight | Degree of alkyl substitution | $E^1$ | A | n | $E^2$ | R | Degree of substitution |
| Compound 1 | EPS-11 | Hydroxyethyl cellulose (UCC) | 1,500,000 | 1.8 | 2-hydroxy-trimethylene | Ethylene | 12 | —O— | -n$C_{12}H_{25}$ | 0.004 |
| Compound 2 | EPS-21 | Hydroxyethyl cellulose (UCC) | 500,000 | 1.8 | 2-hydroxy-trimethylene | Ethylene | 12 | —O— | -n$C_{12}H_{25}$ | 0.004 |
| Compound 3 | EPS-49 | Hydroxyethyl cellulose (Hercules) | 500,000 | 2.5 | 2-hydroxy-trimethylene | Ethylene | 12 | —O— | -n$C_{12}H_{25}$ | 0.004 |
| Compound 4 | EPS-47 | Hydroxyethyl cellulose (Hercules) | 200,000 | 2.5 | 2-hydroxy-trimethylene | Ethylene | 12 | —O— | -n$C_{12}H_{25}$ | 0.014 |
| Compound 5 | EPS-63 | Hydroxyethyl cellulose (Hercules) | 100,000 | 2.5 | 2-hydroxy-trimethylene | Ethylene | 12 | —O— | -n$C_{12}H_{25}$ | 0.02 |
| Compound 6 | EPS-28 | Hydroxypropyl starch (Nippon Starch Chemical Co., Ltd.) | Unknown | Unknown | 2-hydroxy-trimethylene | Ethylene | 12 | —O— | -n$C_{12}H_{25}$ | 0.007 |
| Compound 7 | — | Hydroxyethyl cellulose (UCC) | 800,000 | 1.8 | 2-hydroxy-trimethylene | Ethylene | 20 | —O— | -n$C_{18}H_{37}$ | 0.003 |
| Compound 8 | EPS-33 | Methyl cellulose (Shin-Etsu Chemical Co., Ltd.) | 1,000,000 | Me1.4 Hydroypropyl 0.2 | 2-hydroxy-trimethylene | Ethylene | 12 | —O— | -n$C_{12}H_{25}$ | 0.004 |
| Compound 9 | EPS-1 | Hydroxyethyl cellulose (UCC) | 1,500,000 | 1.8 | 2-hydroxy-trimethylene | Ethylene | 9 | —O— | -n$C_{12}H_{25}$ | 0.0055 |
| Compound 10 | EPS-31 | Hydroxyethyl cellulose (UCC) | 800,000 | 1.8 | 2-hydroxy-trimethylene | Ethylene | 12 | —O— | -n$C_{12}H_{25}$ | 0.0041 |
| Compound 11 | EPS-35 | Hydroxyethyl cellulose (UCC) | 1,500,000 | 1.8 | 2-hydroxy-trimethylene | Ethylene | 19 | —O— | -n$C_{12}H_{25}$ | 0.004 |
| Compound 12 | EPS-42 | Hydroxyethyl cellulose (Hercules) | 100.000 | 2.5 | 2-hydroxy-trimethylene | Ethylene | 12 | —O— | -n$C_{12}H_{25}$ | 0.004 |
| Compound 13 | EPS-44 | Hydroxyethyl cellulose (UCC) | 500.000 | 1.8 | 2-hydroxy-trimethylene | Ethylene | 15 | —O— | -n$C_{16}H_{33}$ | Unknown |
| Compound 14 | EPS-62 | Hydroxyethyl cellulose (Hercules) | 100.000 | 2.5 | 2-hydroxy-trimethylene | Ethylene | 12 | —O— | -n$C_{12}H_{25}$ | 0.0123 |
| Compound 15 | EPS-41 | Hydroxyethyl cellulose (Hercules) | 200.000 | 2.5 | 2-hydroxy-trimethylene | Ethylene | 12 | —O— | -n$C_{12}H_{25}$ | 0.004 |
| Compound 16 | EPS-46 | Hydroxyethyl cellulose (Hercules) | 200.000 | 2.5 | 2-hydroxy-trimethylene | Ethylene | 12 | —O— | -n$C_{12}H_{25}$ | 0.009 |
| Compound 17 | SPS-K1 | Hydroxyethyl cellulose (UCC) | 1.500.000 | 1.8 | 2-hydroxy-trimethylene | — | 0 | —O— | -n$C_{18}H_{37}$ | 0.0032 |
| Compound 18 | SPS-S | Hydroxyethyl cellulose (Hercules) | 1.500.000 | 2.5 | 2-hydroxy-trimethylene | — | 0 | —O— | -n$C_{18}H_{37}$ | 0.0037 |
| Compound 19 | — | Hydroxyethyl cellulose (UCC) | 800.000 | 1.8 | —$(CH_2)_3$CO— | Ethylene | 50 | —O— | -n$C_8H_{17}$ | 0.010 |

TABLE 1-continued

| Compound | Code number | Backbone (Cellulose ether or starch ether) | | | Substituent [-E$^1$-(OA)$_n$E$^2$-R—] | | | | | |
|---|---|---|---|---|---|---|---|---|---|---|
| | | Substance | Average molecular weight | Degree of alkyl substitution | E$^1$ | A | n | E$^2$ | R | Degree of substitution |
| Compound 20 | — | Potato starch (Katayama Chemical, Inc.) | — | — | 2-hydroxy-trimethylene | Ethylene | 10 | —O— | -nC$_{12}$H$_{25}$ | 0.005 |
| Compound 21*[1] | POLY SURF67 | Hydroxyethyl cellulose | Unknown | Unknown | Unknown | Unknown | 0 | Unknown | Unknown | Unknown |
| Compound 22*[2] | PLUS 330CS | Hydroxyethyl cellulose | Unknown | Unknown | Unknown | Unknown | 0 | Unknown | Unknown | Unknown |

*[1]POLY SURF 67 (manufactured by Hercules Incorporated),
*[2]PLUS 330CS (manufactured by Hercules Incorporated

Example 1

(1) The polysaccharide derivative of the present invention was dissolved in distilled water to prepare 1% solution. Quantity of *Dermatophagoides allergen* was measured as a typical allergen in the indoor environment by sandwich ELISA using a mouse monoclonal antibody. More specifically, quantity of *Dermatophagoides allergen* Derf2 was measured by using Derf2 antibody and a labeled antibody manufactured by Asahi Brewery, Ltd.

The allergen inactivation effect is indicated in terms of the ratio in relation to the control wherein the sample was treated in the same way except for the use of distilled water, namely, by assuming the Derf2 quantity in the control as 1.

(2) Scratch extract "mite" (manufactured by Torii Pharmaceutical Co., Ltd.) was placed in a dialysis tube, and dialyzed overnight in 10% PBS (4° C.) to remove glycerol in the extract. The thus dialyzed mite extract was adjusted to a concentration of 0.5 mg/mL with PBS. 50 μL of this mite extract and 50 μL of 1% sample solution prepared with distilled water were placed in a 1.5 mL siliconized microtube, and the mixture was stirred with vortex and allowed to stand at room temperature for 2 hours. For the control, the sample was replaced with distilled water of the same volume. 1% tannic acid of the same volume was used for the positive control. The reaction was then terminated by adding 400 μL of 11.25% BSA (dissolved in PBS) to the tube, and centrifugation was conducted at 15,000 rpm at room temperature for 10 minutes. The supernatant was used for ELISA. Quantity of Derf2 in the reaction solution was determined by using anti-Derf2 monoclonal antibody (15E11) and HRP-labeled anti-Derf2 monoclonal antibody (13A4) manufactured by Asahi Brewery, Ltd. in accordance with the protocol attached with the product, and using Derf2 for the Derf2 antigen for depicting the calibration curve.

Quantity of the Derf2 treated with various samples was calculated in relation to the quantity of Derf2 treated with the distilled water, which was assumed to be 1. The results are shown in Table 2.

TABLE 2

| Sample | Quantity of Derf2 (Ratio to the control) |
|---|---|
| Compound of the invention | |
| Compound 9 | 0.6 |
| Compound 1 | 0.6 |
| Compound 6 | 0.4 |
| Compound 10 | 0.6 |
| Compound 11 | 0.5 |
| Compound 12 | 0.6 |
| Compound 13 | 0.6 |
| Compound 21 | 0.8 |
| Compound 22 | 0.8 |
| Comparative compound | |
| Tannic acid | 0.2 |
| Distilled water | 1.0 |

As described above, the compounds of the present invention were highly effective in inactivating the allergen.

Example 2

Quidel Allergen Screen (manufactured by Xenith Biomed) which is a reagent for detecting antigen-specific IgE antibody by using enzyme-labeled anti-IgE antibody was used to measure the reactivity between the allergen (house dust, *Dermatophagoides farinae, Dermatophagoides pteronyssinus*, cat epidermis, *Cryptomeria japonica*, ragweed, and the like) immobilized on a dip stick and the IgE antibody from the allergy patient by the procedure as described below.

The allergen stick was placed in a wetting box with the pad side facing upward, and the stick was impregnated with the product of the present invention adjusted to 1% at an amount of 100 μL/stick and left at room temperature for 2 hours. Each pad was washed evenly for 30 seconds with physiological saline in a washing bottle, and 50 μL/stick of the serum collected from an allergy patient was added dropwise to the pad and the serum was evenly spread. The wetting box was covered with lid and allowed to stand for 18 hours at room temperature. After the completion of the reaction, the pad was washed evenly for 20 seconds by the physiological saline in a washing bottle.

About 1 mL of enzyme-labeled anti-IgE antibody was placed in a test tube, and allergen stick is placed in the test tube with the pad facing downward after washing the allergen stick and shaking off the excess water, and the reaction was allowed to take place at room temperature for 30 minutes. After the termination of the reaction, each pad was evenly washed with tap water for 2 minutes. At this occasion, disappearance of the red color on the pad was confirmed. About 1 mL of the substrate solution was poured into test tube, and allergen stick was placed in the test tube with the pad facing downward after washing the allergen stick and shaking off the excess water, and the reaction was allowed to take place at room temperature for 30 minutes. After the completion of the reaction, reaction was terminated by absorbing the water impregnated in the pad with a paper towel by gently patting the pad with the paper towel from the rear side of the pad. Next, intensity of the blue color developed was measured with an image analyzer, and decrease in the reactivity by the product of the present invention was calculated by the following equation by using the color intensity attained when the IgE from allergy patient was used with distilled water treatment for the control. The results are shown in Tables 3 and 4.

Allergen inactivation effect (%)=100−{(IgE reaction intensity when treated by the product of the present invention)−(reaction intensity of the negative control)}/{(IgE reaction intensity of the control treated by distilled water)−(reaction intensity of the negative control)×100

TABLE 3

Allergen inactivating effect (%) <Animal allergen>

| Sample | House dust 1 | Dermato- phagoides farinae | Dermato- phagoides pteronys- sinus | Cat epithe- lium |
|---|---|---|---|---|
| Compound of the invention | | | | |
| Compound 1 | 86 | 80 | 90 | 87 |
| Compound 4 | 100 | 100 | 100 | 99 |
| Compound 17 | 52 | 46 | 51 | 48 |
| Compound 18 | 97 | 98 | 98 | 96 |
| Compound 14 | 99 | 98 | 97 | 98 |
| Compound 2 | 99 | 95 | 95 | 97 |
| Compound 15 | 97 | 89 | 85 | 97 |
| Compound 16 | 99 | 81 | 82 | 97 |
| Compound 3 | 100 | 97 | 96 | 100 |
| Compound 21 | 92 | 87 | 86 | 98 |
| Compound 22 | 62 | 62 | 60 | 77 |
| Comparative compound | | | | |
| Tannic acid | 83 | 62 | 70 | 92 |
| Smectite | 40 | 31 | 55 | 23 |
| Distilled water | 0 | 0 | 0 | 0 |

TABLE 4

Allergen inactivating effect (%) <Plant allergen>

| Sample | Ceder | Ragweed |
|---|---|---|
| Compound of the invention | | |
| Compound 1 | 70 | 99 |
| Compound 4 | 90 | 100 |
| Comparative compound | | |
| Tannic acid | 78 | Nd |
| Smectite | 50 | 75 |
| Distilled water | 0 | 0 |

As described above, the compound of the present invention had high allergen reducing effect.

Example 3

Production of Mask for Pollinosis

Materials used in commercially available masks such as gauze and nonwoven are impregnated with Preparation 1 as shown below containing the compound of the present invention (Compound 1, Compound 3, Compound 4, Compound 14, or Compound 21) at an amount approximately 3 times larger than the material, and the impregnated materials are dried or semi-dried to produce the mask for pollinosis. Use of such mask is effective in catching and detoxicating the pollen.

<Preparation 1>

| | |
|---|---|
| The compound of the present invention | 1% |
| 1,3-butylene glycol | 20% |
| Methyl paraoxybenzoate | 0.2% |
| Piroctone olamine | 0.1% |
| Sodium benzoate | 0.2% |
| Lysine | 1.0% |
| Flavor | 0.1% |
| Purified water | the balance |

Example 4

Production of Sheet for Pollinosis Mask

A sheet for pollinosis mask can be produced by impregnating a sheet of nonwoven used for the mask with Preparation 1 as described above of the amount approximately 3 times the mass of the sheet, and drying or semi-drying the sheet. Use of such sheet by sandwiching the sheet between the mask or by covering the mouth with the sheet is effective in catching and detoxicating the pollen.

Example 5

Spraying Solution for Mask

Preparation 2 as shown below containing the compound of the present invention (Compound 1, Compound 3, Compound 4, Compound 14 or Compound 21) is produced to use the preparation as a solution for spraying the mask. Spraying of this spraying solution on a commercially available mask and using the mask after drying realizes effects equivalent to those of the pollinosis mask and the sheet for pollinosis mask as described above.

<Preparation 2>

| | |
|---|---|
| The compound of the present invention | 0.5% |
| 55% ethanol | 50% |
| Glycerin | 2% |
| Flavor | 0.1% |
| Purified water | the balance |

Example 6

Cosmetic Product

Cosmetic products containing the compounds of the present invention (Compound 1, Compound 3, Compound 4, Compound 14, Compound 17, Compound 18 or Compound 21) and having the formulation as shown in (1) and (2) below are produced by the method commonly used in the art. By applying these cosmetic products on the skin, mite allergen which is the cause of atopic dermatitis can be detoxicated on the skin to thereby prevent the onset of dermatitis or improve the dermatitis.

| (1) Protective cream | |
| --- | --- |
| The compound of the present invention | 1 g |
| Cholesterol | 0.5 g |
| Cholestearyl isostearate | 1 g |
| Polyether modified silicone | 1.5 g |
| Cyclic silicone | 20 g |
| Methylphenyl polysiloxane | 2 g |
| Methyl polysiloxane | 2 g |
| Magnesium sulfate | 0.5 g |
| 55% ethanol | 5 g |
| Carboxymethyl chitin | 0.5 g |
| Ceramide | 0.5 g |
| Purified water | balance/total 100 g |
| (2) Protective lotion | |
| The compound of the present invention | 2 g |
| Sodium pyrroridonnecarboxylate | 1 g |
| Polyoxyethylene (20) sorbitan monolaurate | 1.5 g |
| Glycerin | 2 g |
| Purified water | balance/total 100 g |

Example 7

Production of Wiper Sheet

A core/shell structure containing the core of polypropylene and the shell of polyethylene which is formed with 3D crimps (2.8 dtex×51 mm; melting point of the shell component, 130° C.) was used to produce an air through nonwoven having a grammage of 27 g/m². The fibers were thermally bonded at a temperatures of 140° C. The air through nonwoven had a breaking strength of 1660 cN/25 mm in the machine direction (MD) and 220 cN/25 mm in the cross direction (CD).

In the meanwhile, rayon fiber (1.7 dtex×40 mm), acrylic fiber (0.9 dtex×51 mm), and core/shell fiber containing the core of polypropylene and the shell of polyethylene (1.0 dtex×38 mm) were mixed at a weight ratio of 50/25/25, and fiber webs having a grammage of 19 g/m² were produced by conventional carding machine. The fiber web was placed on both sides of the air through nonwoven as described above, and the laminate was subjected to water needling under low energy conditions to thereby intertwine the air through nonwoven and the fiber web to produce a complex spunlace nonwoven having a grammage of 65 g/m² with surface layers of high fiber freedom. The thus produced nonwoven was embossed with diagonal lattice pattern by using an ultrasound embosser to produce the sheet member.

The thus produced nonwoven was impregnated with an aqueous detergent containing an allergen reducing agent (viscosity: 700 mPa·s/25° C.) wherein weight ratio of water/allergen reducing agent/ethanol/2-amino-2-methyl-1-propanol/dodecylglucoside (degree of condensation, 1.4)/thickener (Carbopol ETD2020, manufactured by Nikko Chemicals Co., Ltd.)/sodium tri-citrate was 93.501/0.1/6/0.145/0.1/0.12/0.034 (weight ratio) to produce a wiper sheet for floor. The allergen reducing agent was produced by the Compound 4 of the Production Example. The nonwoven was impregnated with the aqueous detergent at an amount of 250% in relation to the weight of the nonwoven. Carbopol ETD2020 is an acrylates/alkyl methacrylate ($C_{10}$ to $C_{30}$) copolymer. The wiper sheet after the impregnation with the aqueous detergent had a breaking strength of 3120 cN/25 mm in the machine direction (MD) and 410 cN/25 mm in the cross direction (CD).

Example 8

On each side of the resin net (polypropylene lattice net with the distance between the fibers of 8 mm and fiber diameter of 300 μm) was placed a fiber web that had been produced by mixing polyester fiber (1.6 dtex×51 mm), rayon fiber (1.7 dtex×44 mm), and acrylic fiber (0.9 dtex×51 mm) at a weight ratio of 50/25/25 and forming the mixture into a fiber web having a grammage of 30 g/m² with a conventional carding machine. Next, the laminate was subjected to water needling under low energy conditions and formed into the shape of substrate to thereby obtain the a nonwoven (sheet member). The resulting nonwoven was impregnated with the detergent containing the allergen reducing agent used in Example 1 (viscosity 700 mPa·s/25° C.) at an amount of 250% in relation to the weight of the nonwoven. The wiper sheet after the impregnation with the aqueous detergent had a breaking strength of 3833 cN/25 mm in the machine direction (MD) and 1182 cN/25 mm in the cross direction (CD).

Comparative Example 1

A wiper sheet was produced by repeating the procedure of Example 7 except that the sheet was not impregnated with the detergent containing the allergen reducing agent.

Comparative Example 2

A wiper sheet was produced by repeating the procedure of Example 8 except that the sheet was not impregnated with the detergent containing the allergen reducing agent.

The resulting wiper sheet was evaluated for the wiping performance as described in 1) to 8), below.

1) Amount of Detergent Released

The wiper sheet was mounted on Quickle Wiper (manufactured by Kao Corporation), and amount of the detergent released per 1 tatami mat unit was measured by wiping 6 tatami mat units of floor. The wiper sheet was removed from the cleaning head after wiping each tatami mat unit and weighed to measure the amount of detergent. The floor was cleaned by wiping the floor back and forth, and the wiping back and forth for a distance of about 90 cm is referred as 1 stroke. 2 strokes of wiping in the longitudinal direction (180 cm) and 4 strokes of wiping in the width direction (90 cm) were conducted per 1 tatami mat unit.

2) Static Frictional Resistance Value as an Index for Freeness of the Fiber in the Surface Layer of the Wiper Sheet The measurement was conducted by the procedure as described above. It is to be noted that the load of 400 g substantially corresponds to the average load applied to the wiper sheet when a floor is cleaned by the wiper sheet mounted on Quickle Wiper (manufactured by Kao Corporation).

3) Area (%) of the Projection

The measurement was conducted by the procedure as described above.

4) Hair Catching Ability (%)

The wiper sheet was mounted on Quickle Wiper (manufactured by Kao Corporation). 5 hairs each having a length of about 10 cm were scattered on a piece of flooring board (Woody Tile MT613T manufactured by Matsushita Electric Works, Ltd., 30 cm×30 cm), and the tile was wiped for 2 strokes (60 cm) with the wiper sheet placed on the tile to thereby measure the number of hair caught by the wiper sheet. This procedure was repeated 6 times to calculate the number of hairs caught out of 30 hairs. The number of hairs caught was divided by 30 and then multiplied by 100 to calculate the hair catching ability in percentage.

5) Dust Catching Ability

The wiper sheet was mounted on Quickle Wiper (manufactured by Kao Corporation). 0.1 g of 7 types of test dusts according to JIS (Kanto loam, small grain) were uniformly distributed on a piece of wood flooring tile (Woody Tile MT613T manufactured by Matsushita Electric Works, Ltd., 100 cm×100 cm) with brush, and the flooring tile was cleaned by wiping back and forth for 4 strokes. This procedure was repeated 6 times and the wiper sheet after the use was dried to measure the weight (the sheet+involatile content in the detergent+the dust). Weight of the dust caught was calculated by subtracting the weight of the sheet before the impregnation of the detergent and theoretical weight of the remaining involatile content of the detergent. The weight of the dust was divided by the weight of the total weight of the distributed dust (0.6 g=0.1 g×6 times) and multiplied by 100 to determine the dust catching ability in percentage.

6) Ability to Remove Dried Staining of Soy Sauce in the Cleaning of 6th Tatami Mat Unit 1 drop (0.02 g) of commercially available soy sauce was dropped on a flooring (area, 1 tatami mat unit) and dried with a dryer. The wiper sheet was mounted on Quickle Wiper (manufactured by Kao Corporation), and after continuously wiping 5 tatami mat units of clean flooring, the flooring of 1 tatami mat unit with the dry stain of the soy sauce was cleaned with the same wiper sheet for evaluation by the criteria as described below. The clean floor of the first 5 tatami mat units that was cleaned first was cleaned by the same procedure as the one used in the measurement of the released detergent amount, and in the subsequent cleaning of the flooring with the dry soy sauce stain, only the stained part was wiped to evaluate the number of strokes in relation to the stain removal.

A: The stain was completely removed by the cleaning of up to 10 strokes.

A to B: The stain was completely removed by the cleaning up to 15 strokes.

B: The stain was completely removed by the cleaning of up to 20 strokes.

B to C: The stain was completely removed by the cleaning of up to 30 strokes.

D: The stain was not completely removed by the cleaning of more than 30 strokes.

7) Finishing

The wiper sheet was mounted on Quickle Wiper (manufactured by Kao Corporation) and a clean floor of 100 cm×100 cm was cleaned. Finishing of the flooring after drying was visually evaluated under fluorescent lamp by using the following 3 level rating scale.

A: No marks (wipe marks etc.) of the residual component are found.

B: Some marks (wipe marks etc.) of the residual component are found.

C: Marks (wipe marks etc.) of the residual component are significant.

8) Handling of the Wiper in the Cleaning of the 1st Tatami Mat Unit and the Load Applied to the Wiper at the Start of the Wiping The wiper sheet was mounted on Quickle Wiper (manufactured by Kao Corporation) and handling of the wiper at the start of the wiping of the flooring board (Woody Tile E type, KER501 manufactured by Matsushita Electric Works, Ltd.) with one hand was visually evaluated by using the following 4 level rating scale.

A: Substantially no resistance is felt.

A to B: The floor can be wiped with single hand although some resistance is felt.

B: The floor can be wiped with single hand although considerable resistance is felt.

C: Substantial resistance is felt, and the wiper handle deflects when wiped by one hand.

Figure 4:
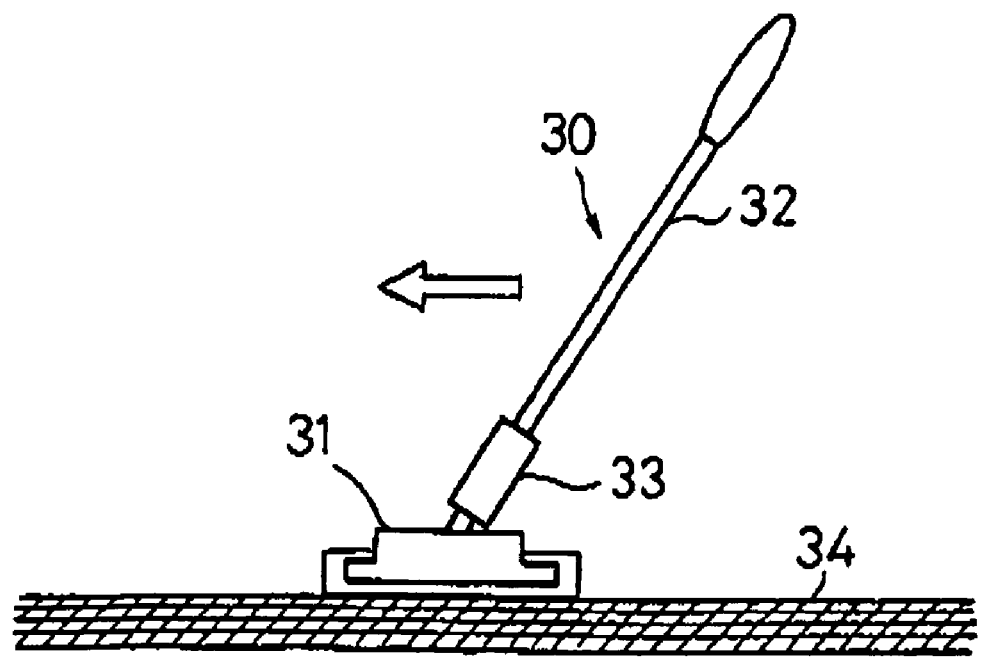
FIG. 4 is a schematic view showing the procedure of measuring the load required for moving the wiper at the start of the wiping.

As shown in FIG. 4, a load cell 33 for measuring compressive load was mounted on the Quickle Wiper 30 between the cleaning head 31 and the handle 32, and the compressive load applied at the start of the wiping of the flooring 34 by using this Quickie Wiper 30 was measured.

[Evaluation of Allergen Inactivating Effect]

Pollen removing effect was determined by the procedure as described below, and the allergen reducing effect was evaluated by using a 4 level rating scale.

50 mg of *Cryptomeria japonica* pollen was distributed on the surface of a glass plate (30 cm×30 cm), and the plate was wiped with the wiper sheet produced as described above. The pollen remaining on the glass plate was washed with 50 mL of the phosphate buffer solution ($KH_2PO_4$, NaCl, and $Na_2PO_4.7H_2O$ dissolved in distilled water at 0.144 g/L, 9.00 g/L, and 0.795 g/L, respectively) adjusted to pH 7.4±0.1. (The thus determined amount of the pollen is referred to as "amount of the remaining pollen")

<Measurement of the Amount of Pollen Allergen>

Amount of Cry j1 and Cry j2 in the sample was measured by the procedure as described below, and sum of the amounts measured was used as the amount of *Cryptomeria japonica* pollen allergen in the sample.

[Measurement Using Cry j1 ELISA]

1. Monoclonal antibody Ab-Cry j1 mAb 013 (manufactured by Seikagaku Corporation) is diluted with PBS to a concentration of 2 μg/mL, and the solution is dispensed in the wells of a microplate (manufactured by Sumitomo Bakelite Co., Ltd., Elisa Plate H Type) at 50 μL/well and allowed to stand at room temperature for 2 hours.

2. The microplate is washed three times with PBS.

3. PBS supplemented with 1% BSA (Block Ace manufactured by Dainippon Pharmaceutical Co., Ltd.) is dispensed in the well at 200 μL/well and allowed to stand at room temperature for 1 hour for blocking.

4. The microplate is washed three times with PBS containing 0.05% by mass of Tween 20 (SIGMA) (hereinafter referred to as T-PBS).

5. Standard is prepared by diluting purified Cry j1 (manufactured by Seikagaku Corporation) from 4 ng/mL to 2n folds by n=5 tubes of T-PBS, and the solution is then dispensed in the well at 50 μL/well. Negative control is also prepared by adding 50 μL of T-PBS instead of the Cry j1. The sample measured is dispensed in the well at 50 μL/well after adequately diluting with T-PBS, and allowed to stand at room temperature for 2 hours.

6. The microplate is washed three times with T-PBS.

7. Peroxidase conjugated Ab-Cry j1 mAb 053 (manufactured by Seikagaku Corporation) is dispensed in the well at 50 μL/well at optimal concentration, and allowed to stand at room temperature for 2 hours.

8. The microplate is washed three times with T-PBS.

9. Color is developed by using a chromogenic kit for peroxidase (manufactured by Sumitomo Bakelite Co., Ltd.). First, 0.1 mL of substrate solution is added to 10 mL of chromogenic agent to prepare the chromogenic solution, and this chromogenic solution is dispensed in the well at 100 μL/well for color development at room temperature. Termination solution is then added at 100 μL/well to stop the reaction, and the absorption at 450 nm is measured by a plate reader.

10. Cry j1 concentration of the sample measured is calculated by using the calibration curve depicted by using the absorption of the standard.

[Measurement Using Cry j2 ELISA]

1. Monoclonal antibody Ab-Cry j2 mAb T27 (manufactured by Seikagaku Corporation) is diluted with PBS to a concentration of 2 μg/mL, and the solution is dispensed in the wells of a microplate (manufactured by Sumitomo Bakelite Co., Ltd., Elisa Plate H Type) at 50 μL/well and allowed to stand at room temperature for 2 hours.

2. The microplate is washed three times with PBS.

3. PBS supplemented with 1% BSA (Block Ace manufactured by Dainippon Pharmaceutical Co., Ltd.) is dispensed in the well at 200 μL/well and allowed to stand at room temperature for 1 hour for blocking.

4. The microplate is washed three times with T-PBS.

5. Standard is prepared by diluting purified Cry j2 (manufactured by Seikagaku Corporation) from 10 ng/mL to 2n folds by n=5 tubes of T-PBS, and the solution is then dispensed in the well at 50 μL/well. Negative control is also prepared by adding 50 μL of T-PBS instead of the Cry j2. The sample measured is dispensed in the well at 50 μL/well after adequately diluting with T-PBS, and allowed to stand at room temperature for 2 hours.

6. The microplate is washed three times with T-PBS.

7. Peroxidase conjugated Ab-Cry j2 pAb (manufactured by Seikagaku Corporation) is dispensed in the well at 50 μL/well at optimal concentration, and allowed to stand at room temperature for 2 hours.

8. The microplate is washed three times with T-PBS.

9. Color is developed by using a chromogenic kit for peroxidase (manufactured by Sumitomo Bakelite Co., Ltd.). First, 0.1 mL of substrate solution is added to 10 mL of chromogenic agent to prepare the chromogenic solution, and this chromogenic solution is dispensed in the well at 100 μL/well for color development at room temperature. Termination solution is then added at 100 μL/well to stop the reaction, and the absorption at 450 nm is measured by a plate reader.

10. Cry j2 concentration of the sample measured is calculated by using the calibration curve depicted by using the absorption of the standard.

Pollen reducing ability was calculated according to the following equation by using the amount of the pollen (*Cryptomeria japonica*) allergen determined as described above. The pollen reducing ability was evaluated by using the following four level rating scale using the calculated value for the index.

Pollen reducing ability (%)={(Amount of the remaining pollen/Amount of the remaining pollen in Comparative Example 1)}×100

A: Pollen reducing ability is less than 30%.

B: Pollen reducing ability is 30% or more but less than 50%.

C: Pollen reducing ability is 50% or more but less than 80%.

D: Pollen reducing ability is 80% or more.

TABLE 5

| Sheet constitution | Example 7 Combination of spunlace | Example 8 Spunlace with inserted net | Comparative Example 1 Combination of spunlace | Comparative Example 2 Spunlace with inserted net |
|---|---|---|---|---|
| Embossing | Yes | No | Yes | No |
| Projection area (%) | 65 | 70 | 65 | 70 |
| Breaking strength (cN/25 mm) | | | | |
| Machine direction MD | 3120 | 3833 | 3205 | 3845 |
| Cross direction CD | 410 | 1182 | 420 | 1165 |
| Detergent | | | | |
| Viscosity (mPa · s/25° C.) | 700 | 700 | 500 | 500 |
| Allergen reducing agent (wt %) | 0.1 | 0.1 | 0 | 0 |
| Nonvolatile residual component (%) | 0.4 | 0.4 | 0.3 | 0.3 |
| Detergent releasing amount (g) | 0.89 | 1.02 | 0.90 | 0.95 |
| Static frictional resistance value of the sheet (cN) | | | | |
| Machine direction MD | 1405 | 1385 | 1413 | 1398 |
| Cross direction CD | 1395 | 1402 | 1404 | 1413 |
| Percentage of the hair caught (%) | 90 | 87 | 87 | 90 |
| Percentage of the dust caught (%) | 87 | 89 | 87 | 89 |
| Capability of removing dried soy sauce in 6th tatami mat | A | A | A | A |
| Finishing | A | A | A | A |
| Handling convenience of the wiper in cleaning 1st tatami mat (load at the start of pushing) | A | A | A | A |
| Allergen reducing performance | A (21%) | A (23%) | D (100%) | D (95%) |

As shown in Table 5, the wiper sheets of the Examples (of the present invention) evidently reduce the allergen on the surface of the objects wiped by the sheet to a degree higher than the wiper sheets of the Comparative Examples.

The invention claimed is:

1. A method for inactivating allergen comprising treating an allergen-existing environment with an allergen inactivating agent comprising a polysaccharide derivative as its effective component, wherein the polysaccharide derivative has a cellulose ether as its backbone, and some or all of hydrogen atoms in the hydroxy group of the polysaccharide derivative are substituted by a group represented by formula (I):

$$-E^1-(OA)_n-E^2-R \qquad (1)$$

wherein $E^1$ represents an alkylene containing 1 to 6 carbon atoms optionally substituted with a hydroxy group or an oxo group; n represents a number of 0 to 50; A independently represents an alkylene containing 1 to 6 carbon atoms, the number of A being n; $E^2$ represents an ether bond or an oxycarbonyl group; R represents an alkyl group containing 4 to 30 carbon atoms optionally substituted with a hydroxy group, a sulfoalkyl group containing 1 to 5 carbon atoms optionally substituted with a hydroxy group, or a salt thereof, comprising spraying the polysaccharide derivative in an allergen-existing environment.

2. The method according to claim 1, wherein the cellulose ether is hydroxyethyl cellulose.

3. The method according to claim 1, wherein the cellulose ether has an average molecular weight of 10,000 to 2,000,000.

4. The method according to claim 1, wherein the cellulose ether has an average molecular weight of 50,000 to 1,500,000.

5. The method according to claim 1, wherein the cellulose ether has an average molecular weight of 100,000 to 600,000.

6. A method for inactivating allergen comprising treating an allergen-existing environment with an allergen inactivating agent comprising a polysaccharide derivative as its effective component, wherein the polysaccharide derivative has a cellulose ether as its backbone, and some or all of hydrogen atoms in the hydroxy group of the polysaccharide derivative are substituted by a group represented by formula (I):

$$-E^1-(OA)_n-E^2-R \qquad (1)$$

wherein $E^1$ represents an alkylene containing 1 to 6 carbon atoms optionally substituted with a hydroxy group or an oxo group; n represents a number of 0 to 50; A independently represents an alkylene containing 1 to 6 carbon atoms, the number of A being n; $E^2$ represents an ether bond or an oxycarbonyl group; R represents an alkyl group containing 4 to 30 carbon atoms optionally substituted with a hydroxy group, a sulfoalkyl group containing 1 to 5 carbon atoms optionally substituted with a hydroxy group, or a salt thereof, comprising spraying the polysaccharide derivative on a mask.

7. The method according to claim 6, wherein the cellulose ether has an average molecular weight of 10,000 to 2,000,000.

8. The method according to claim 6, wherein the cellulose ether has an average molecular weight of 50,000 to 1,500,000.

9. The method according to claim 6, wherein the cellulose ether has an average molecular weight of 100,000 to 600,000.

* * * * *

UNITED STATES PATENT AND TRADEMARK OFFICE
CERTIFICATE OF CORRECTION

PATENT NO. : 8,133,991 B2  Page 1 of 1
APPLICATION NO. : 11/045328
DATED : March 13, 2012
INVENTOR(S) : Mami Nonomura et al.

It is certified that error appears in the above-identified patent and that said Letters Patent is hereby corrected as shown below:

Column 29, line 8, "weight of 10,000 to 2,000,", should read --weight of--;
line 9, "000.", should read --10,000 to 2,000,000.--;
line 11, "weight of 50,000 to 1,500,", should read --weight of--;
line 12, "000.", should read --50,000 to 1,500,000.--.

Column 30, line 13, "weight of 10,000 to 2,000,", should read --weight of--;
line 14, "000.", should read --10,000 to 2,000,000.--;
line 16, "weight of 50,000 to 1,500,", should read --weight of--;
line 17, "000.", should read --50,000 to 1,500,000.--.

Signed and Sealed this
Twelfth Day of June, 2012

David J. Kappos
*Director of the United States Patent and Trademark Office*